(12) United States Patent
Reeves et al.

(10) Patent No.: US 7,336,348 B2
(45) Date of Patent: *Feb. 26, 2008

(54) APPARATUS AND METHOD FOR DETERMINING THE VIABILITY OF EGGS

(75) Inventors: Sidney James Reeves, Rose In Valley, Lower Hugus Road, Threemilestone, Truro (GB) TR3 6BD; Keith Angus Simpson, Torquay (GB)

(73) Assignee: Sidney James Reeves, Cornwall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/562,128

(22) Filed: Nov. 21, 2006

(65) Prior Publication Data
US 2007/0125305 A1    Jun. 7, 2007

Related U.S. Application Data

(63) Continuation of application No. 10/475,229, filed as application No. PCT/GB02/01784 on Apr. 17, 2002, now Pat. No. 7,154,594.

(30) Foreign Application Priority Data
Apr. 20, 2001    (GB) .................................. 0109765.8

(51) Int. Cl.
*A01K 43/00*    (2006.01)
*G01N 33/06*    (2006.01)

(52) U.S. Cl. ......................................... 356/52; 356/53
(58) Field of Classification Search ..................... None
See application file for complete search history.

(56) References Cited

U.S. PATENT DOCUMENTS 7,154,594 B2 * 12/2006 Reeves et al. ................ 356/52

FOREIGN PATENT DOCUMENTS

JP        2001-013065        1/2001

* cited by examiner

*Primary Examiner*—Michael P. Stafira
(74) *Attorney, Agent, or Firm*—Anthony R. Barkume, PC

(57) ABSTRACT

An apparatus (10) for determining the viability of an egg, which apparatus (10) comprises shielding means (12, 14), emitting means (30) and detecting means (32), the arrangement being such that, in use, the shielding means (12, 14) inhibits exposure of an egg to background infra-red radiation, said emitting means (30) can emit electromagnetic radiation at infra-red wavelength(s) to impinge on the egg, and the detecting means (32) are positioned to detect at least a part of said electromagnetic radiation that has passed through the egg, the apparatus further comprising means for processing an output signal of the detecting means to determine whether there is a cyclical variation in the intensity of the infra-red radiation leaving the egg corresponding to action of a heart, the existence of said cyclical variation indicating that the egg is viable.

24 Claims, 8 Drawing Sheets

Non-viable:

Healthy

Poor signal

APPARATUS AND METHOD FOR DETERMINING THE VIABILITY OF EGGS

FIELD OF INVENTION

The present invention relates to an apparatus and method for determining the viability of eggs laid by egg-laying animals, and in particular but not exclusively, to eggs laid by reptiles and birds, for example parrots.

BACKGROUND

Once an egg has been laid by an animal, it must undergo a period of incubation, either naturally or artificially, during which time development of the young animal takes place. Many birds for example, sit on an egg or clutch of eggs in order to regulate temperature and humidity around the egg(s), such regulation being crucial for the survival and proper development of the embryo inside each egg. Other animals utilise different sources, for example solar or geothermal energy, for this purpose. Alternatively, incubation may be carried out and/or assisted by man. Man-made incubators are well known that can hold a number of eggs and which provide artificial temperature and humidity regulation of the air around the eggs.

Many breeders and conservationists of egg-laying animals need to know whether or not the embryo is alive and developing at the proper rate inside the egg. Such knowledge is required throughout the incubation period, and is important both in natural and artificial incubation scenarios in order to maximise the chances of survival of the young. In natural incubation, for example a clutch of eggs brooded by a bird, if one or more embryos does not survive, those eggs can become infected by bacteria and endanger the remaining eggs. Furthermore, some species of parrot for example the Palm Cockatoo, Black Cockatoo and Hyacinthine Macaw, can only lay fertile eggs during a short period of time each year and even then only incubate one egg at a time. If that egg does not survive, the opportunity for successful breeding has been missed for that year. Such scenarios can have serious implications for endangered species, and for breeders and keepers of such birds who exchange them for considerable sums of money. The situation is analogous for many species of egg-laying animal.

At present there are two well known methods for checking the fertility and development of eggs. The first method, known as "candling", involves placing an egg in front of an intense light source, for example tungsten halogen, so that the inside of the egg is visible to the naked eye, and looking for signs of growth e.g. vein development that is first visible after approximately four days in parrot eggs. Over the next few days it is possible to check for further growth by looking for increasing numbers and density of veins and a growing "dark spot" in the centre of the egg. However, there are three disadvantages with "candling", the first being that a high intensity of light is required to see into the egg meaning that it is exposed to high temperature levels that can damage or kill the embryo in the egg if held over the light for too long. Secondly, the "dark spot" grows at such a rate that after approximately twelve days (in parrot eggs) it occupies so much of the volume of the egg that the veins are no longer visible and it is not possible to tell whether or not the young bird is alive. Thirdly, some eggs are not suitable for "candling" such as raptors, falcons, ducks and wild fowl, whose eggs range from dark green to dark brown in colour, and other species whose shells are so dense that the light from the lamp cannot pass through them. For such eggs it is not possible to tell whether or not they are fertile and alive in the first few days.

The second known method addresses the second and third problems mentioned above. This method involves floating the egg in still warm water and waiting for the egg to move as a result of movement of the young animal inside. There are two disadvantages associated with this method, the first being that the method is unreliable and slow since it relies on a parameter that is inherently random. Secondly, immersing the egg in water exposes it to bacteria that can pass through the shell, particularly as the egg is withdrawn from the water, when water on the surface of the egg tends to be "sucked" in through the pores of the shell severely reducing the egg's ability to self-regulate humidity. Once inside the shell the bacteria and water are in an ideal environment at 37.degree. C. to multiply, potentially endangering the life of the young animal.

U.S. Pat. No. 5,745,228 discloses an apparatus for distinguishing live from infertile poultry eggs at high speed in the presence of ambient (or background) light. The apparatus comprises a photoemitter for emitting infra-red radiation located directly opposite a photodetector. In use eggs pass at high speed (10 inches per second is suggested) between the photoemitter and photodetector on a conveyor. The photodetector is turned on and off 100 times per second in bursts of 250 .mu·s. The photodetector takes readings when the photoemitter is actuated and when deactivated; by subtracting these readings the effects of ambient light on the signal are reduced. The apparatus only has sufficient resolution to classify eggs into three groups namely, clear or early dead, mid dead, and live. These results are not significantly better than can be obtained by the aforementioned method of candling.

FR 2 455 282 discloses an improved candling method in which infra red light is passed through an egg in the presence of background light. Light having passed through the detector is detected and the output signal displayed on a visual display screen. The viability of the egg is determined by comparison of the relative intensity of the received signal either visually or automatically.

However, the disadvantage with the aforementioned publications is that only differences in the received intensity of light from each egg can be compared in order to make an assessment of the viability of an egg.

Thus, it is apparent that there is a need for an apparatus and method of testing the viability of eggs that is more reliable, that minimises the risks to which prior methods have exposed eggs, and which facilitates maximisation of the chances of survival of fertile eggs.

SUMMARY OF THE INVENTION

The present invention is based on an insight into the effect that structures in viable eggs have on infra-red light passing therethrough. This effect is present from approximately 5 to 12 days (depending on the species of animal) up until the animal hatches from the egg.

According to one aspect of the present invention, there is provided an apparatus for determining the viability of an egg, which apparatus comprises shielding means, emitting means and detecting means, the arrangement being such that, in use, the shielding means inhibits exposure of an egg to background infra-red radiation, said emitting means can emit electromagnetic radiation at infra-red wavelength(s) that impinge on the egg, the apparatus further comprising means for processing an output signal of the detecting means to determine whether there is a cyclical variation in the intensity of the infra-red radiation leaving the egg corresponding to action of a heart, the existence of said cyclical variation indicating that the egg is viable.

In one aspect the invention is particularly suitable for use in determining the viability of rare and exotic eggs (e.g. parrots) where speed of determination is less important than the accuracy of the determination.

The use of infra-red light is preferred for two reasons, (1) attenuation of infra-red light passing through eggs is much lower than with light at optical wavelengths, and (2) infra-red light can impinge on the egg for a much longer period without heating the egg. The egg can be damaged by heat when candling with optical light if the egg is left in front of the optical source for too long.

Although the applicant believes that the periodic attenuation of the received radiation will be superimposed on optical light, it is too dangerous to place the egg in front of an optical light source to enable the apparatus of the invention to obtain the cyclical variation. This is because in order to penetrate and pass right through the egg, particularly in dark pigment eggs, light at optical wavelengths must be of such intensity that the egg is in danger of becoming overheated if left near the light source for any appreciable length of time (more than 3 or 4 seconds).

One advantage of at least preferred arrangements is that a user can obtain a virtually instant indication of the viability of the egg i.e. whether it is alive or not. Furthermore, such arrangements mitigate the dangers to which the above mentioned methods have exposed eggs. A further advantage is that much "guesswork" is taken out of prior artificial incubation techniques since the apparatus enables an accurate heart rate of the animal inside the egg to be obtained which indicates whether incubating conditions are optimised. A further advantage is that such arrangements enable the viability of the egg to be determined throughout the incubation period to hatching of the young animal. "Background infra-red radiation" means radiation from unwanted sources, for example artificial lighting and daylight. The applicant has found that the presence of such radiation renders the apparatus difficult to use and inhibits detection of the varying intensity of the radiation that has passed through the egg. The emitting means may emit infra-red at a single wavelength or over a band of wavelengths simultaneously.

Further feature of the apparatus are set out in claims 2 to 11 to which attention is hereby directed.

Advantageously, the detecting means are shielded from detecting electromagnetic radiation emitted directly from said emitting means. This helps to ensure that the output from the detecting means is meaningful. Since some radiation is reflected off the shell of the egg, this shielding also inhibits radiation that has not passed through the egg from reaching the detecting means.

Preferably, the detecting means is positioned to inhibit detection of electromagnetic radiation emitted directly from said emitting means. In one embodiment, the detecting means is shielded by positioning so that, in use, the egg lies between the emitting means and detecting means. In another embodiment, the detecting means is both positioned to inhibit detection of electromagnetic radiation emitted directly from said emitting means and provided with a physical shield.

Advantageously, said emitting means emit electromagnetic radiation over a limited angle. This helps to ensure that the detecting means only detects radiation that has passed through the egg.

Preferably, the limited angle is adjustable. By making the angle adjustable, and hence the amount of infra-red impinging on the egg, a user is able to adjust the apparatus to achieve an optimum output from the detecting means. In one embodiment the apparatus is provided with a plurality of emitting means that each have a different limited angle. In use, a user can switch between each emitting means to obtain the best results.

Advantageously, the emitting means emit electromagnetic radiation in the wavelength range 720 nm to 940 nm.

Preferably, the emitting means emit electromagnetic radiation predominantly at a wavelength of 875 nm. The applicant has found that this produces the strongest outputs from the detecting means with chicken eggs.

Advantageously, the apparatus further comprises a support means for supporting an egg in a position within the apparatus.

Preferably, the detecting means are located adjacent said support means. In one embodiment the detecting means are located within said support means, the arrangement being such that, in use, electromagnetic radiation can reach the detecting means only by passing through the egg. This is particularly advantageous because, in use, the egg and support means enclose the detecting means so that only radiation that has passed through the egg can be detected.

Advantageously, the support means comprises a deformable material that provides a point of contact with an egg, the material deforming to part of the contours of the egg under the egg's weight. This provides a "seal" inhibiting penetration of unwanted infra-red radiation, that might be detected by the detecting means.

Preferably, the deformable material comprises latex. In one embodiment, the latex comprises a black dye. The applicant has found this particularly effective since the combination inhibits penetration of unwanted infra-red radiation and at the same time provides a support that minimises potential for damage to the egg.

Advantageously, the support means are mounted on a base.

Preferably, the base comprises an elastic material, preferably foam rubber, to inhibit damage to an egg should it be dropped onto the base.

Advantageously, the support means comprises a suction cup.

Preferably, said shielding means comprises a housing having a first member and a second member moveable with respect to the first member from a position in which an egg can be inserted into the apparatus to a position in which the egg is shielded from background infra-red radiation. In one embodiment, the detecting means and emitting means are mounted on the first member.

Preferably, the apparatus further comprises a power source. One advantage of this is that the apparatus may be hand-held which makes it easy to use in the field.

According to another aspect of the present invention there is provided a method for determining the viability of an egg, which method comprises the steps of:

(1) placing an egg in an environment that is shielded from background infra-red radiation;

(2) emitting electromagnetic radiation at infra-red wavelength(s) from emitting means toward the egg;

(3) detecting at least a part of said electromagnetic radiation that has passed through the egg with detecting means and generating an output signal therefrom; and (4) processing said output signal to determine whether there is a cyclical variation in the intensity of the infra-red radiation leaving the egg corresponding to action of a heart, the existence of said cyclical variation indicating that the egg is viable.

BRIEF DESCRIPTION OF THE DRAWING

For a better understanding of the present invention, reference will now be made by way of example to the accompanying drawings in which.

DETAILED DESCRIPTION OF THE PREFERRED EMBODIMENTS

Figure 1:
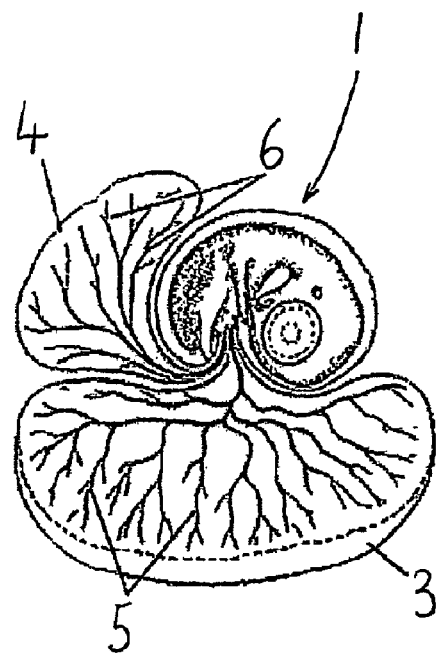
FIG. 1 is a schematic cross section through a seven-day old chicken embryo showing its embryonic membranes and embryonic blood vessels.
Figure 2:
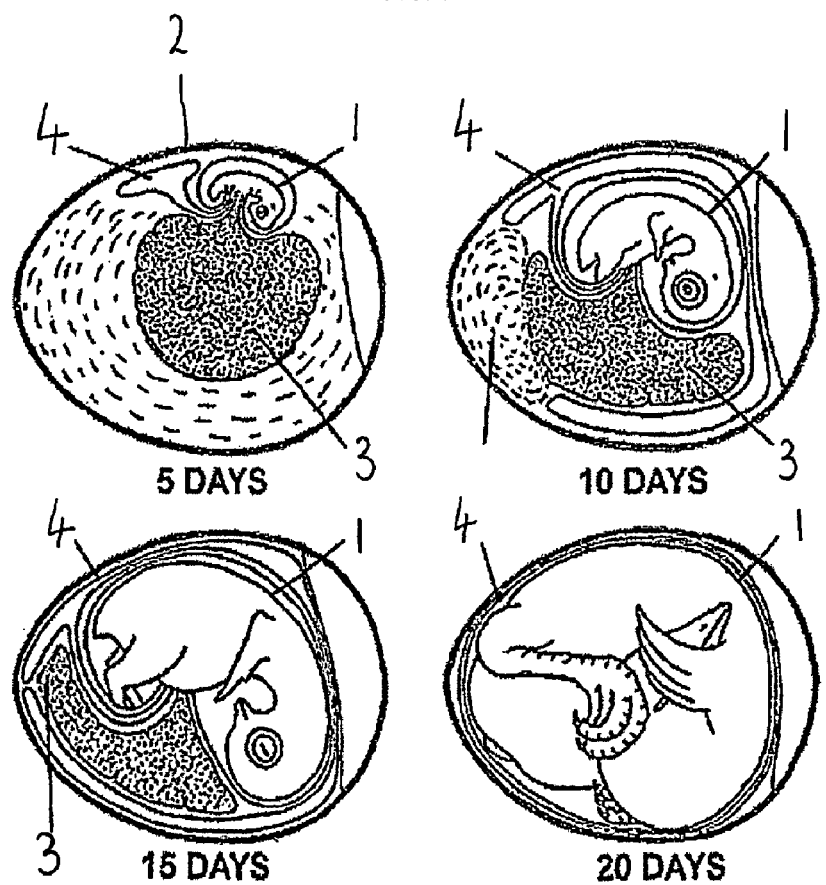
FIG. 2 is a schematic cross section through an egg containing the embryo of FIG. 1 shown at four points during its development.

Referring to FIGS. 1 and 2, for an understanding of the background to the present invention some details of a chicken embryo 1 developing within a shell 2 are shown. It is to be noted that the structure of the chicken egg is very similar to that of a wide variety of egg-laying animals. The embryo 1 comprises a yolk sac 3 within which blood vessels 5, known as the vitelline vessels, extract nutrients and convey them to the embryo. Another structure 4 known as the allantois assists the respiratory cycle of the embryo. As the embryo 1 grows the allantois 4 is pressed against the inner surface of the shell 2 where the capillaries in the allantois can readily exchange carbon dioxide for oxygen that has passed through the pores of the shell. Under action of the animal's heart the blood vessels 6 in the allantois 4 swell and contract in a cyclical fashion. Furthermore, as is apparent from FIG. 2, the allantois 4 grows as the embryo 1 develops so that it covers an increasing surface area adjacent the inner side of the shell 2. The respiratory function of the allantois 4 begins approximately at three to four days from the beginning of the incubation period and ceases when the chick breaks out of the egg and breathes of its own accord. To the best of the applicant's knowledge and belief no apparatus and method has been proposed up to now that takes advantage of the cyclically variable blood flow through the vessels of the allantois and/or the vitelline vessels, caused by the animal's heart, to monitor the viability of the growing embryo within the egg.

Figure 3:
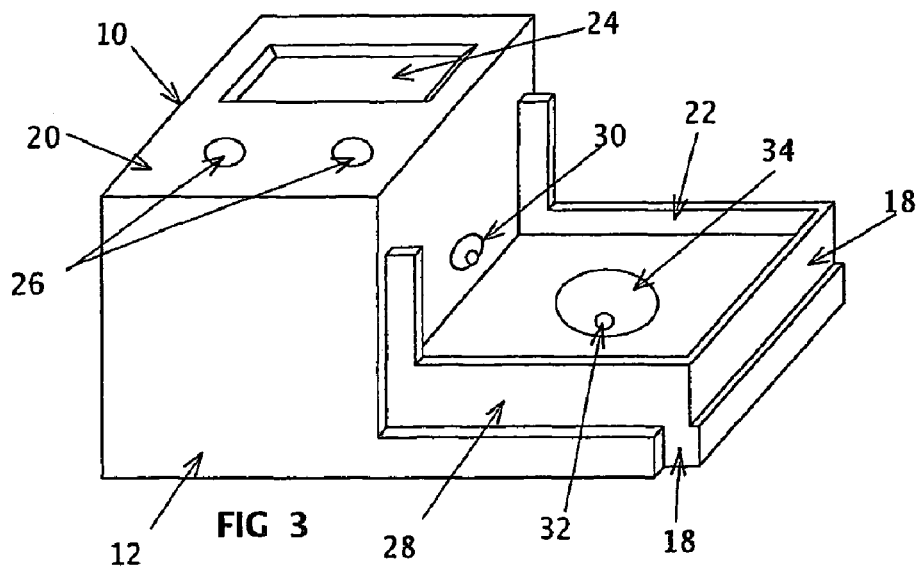
FIG. 3 is a schematic perspective view of part of an apparatus in accordance with the present invention, the lid being removed for clarity.

Referring to FIGS. 3 to 6, an apparatus generally identified by reference numeral 10 comprises a housing 12 and a lid 14. As shown in FIG. 3, the lid 14 can be mounted on the housing 12 via inward projections 16 on the lid 14 that locate with recesses 18 on the housing 12 and permit rotational movement of the lid 14 with respect to the housing 12. The lid 14 is constructed from plastics material that prevents the passage of infra-red radiation through its walls.

The housing 12 comprises two sections, a first section 20 and a second section 22. The first section 20 comprises a liquid crystal display 24, control buttons 26, a power source (not shown) and various electronic processing equipment (not shown) that will be described in greater detail below. The second section 22 comprises a box 28 open at its upper side and having five walls constructed from plastics material that prevent passage of infra-red radiation. Thus, when the lid 14 is in a closed position on the box 28 the volume that is enclosed is shielded from background infra-red radiation. A source 30 is mounted on the box 28 adjacent the second section 22 and is positioned so that it can emit electromagnetic radiation into the box 28. The source 30 is an infra-red (IR) emitter manufactured and sold by Hewlett Packard (part number HSDL-4230) that can emit IR over a wavelength range of 720 940 nm, with peak intensity at approximately 875 nm. It has a power rating of 75 mW/sr at 50 mA and a beam angle of 17.degree., the axis of the beam lying on a perpendicular to plane of the wall on which it is mounted. The applicant has found that the power of infra-red from the source 30 does not appear to cause any damage to the egg under test. An infra-red detector 32 is mounted in the base of box 28 and is designed and positioned to detect IR that has been emitted by the source 30. The detector 32 is manufactured by Texas Instruments as component TSL 250 and is available from Pacer Components (Berkshire, England). It will be noted that the radiation emitted from the source 30 does not directly intersect with the detector 32.

Figure 4:
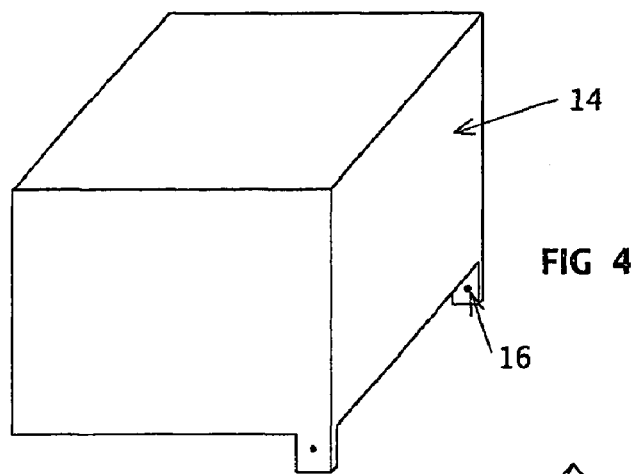
FIG. 4 is a schematic perspective view of a lid suitable for use with the apparatus of FIG. 3.

Mounted on the bottom of the box 28 and around the detector 32 is a holder 34 which comprises an inverted suction cup manufactured from latex so as to be deformable. The suction cup is different to known suction cups in that a black dye has been added during manufacture to inhibit passage of light at infra-red wavelengths. In use, an egg can be placed on and supported by the holder 34 and the latex deforms to the contours of that part of the egg with which it is in contact. The egg can be supported in any orientation by the holder 34. No suction is applied via the holder 34. The distance x as shown in FIG. 4 is 0.05 m, although this does not appear critical and the source 30 may abut an egg or be further away.

Figure 5:
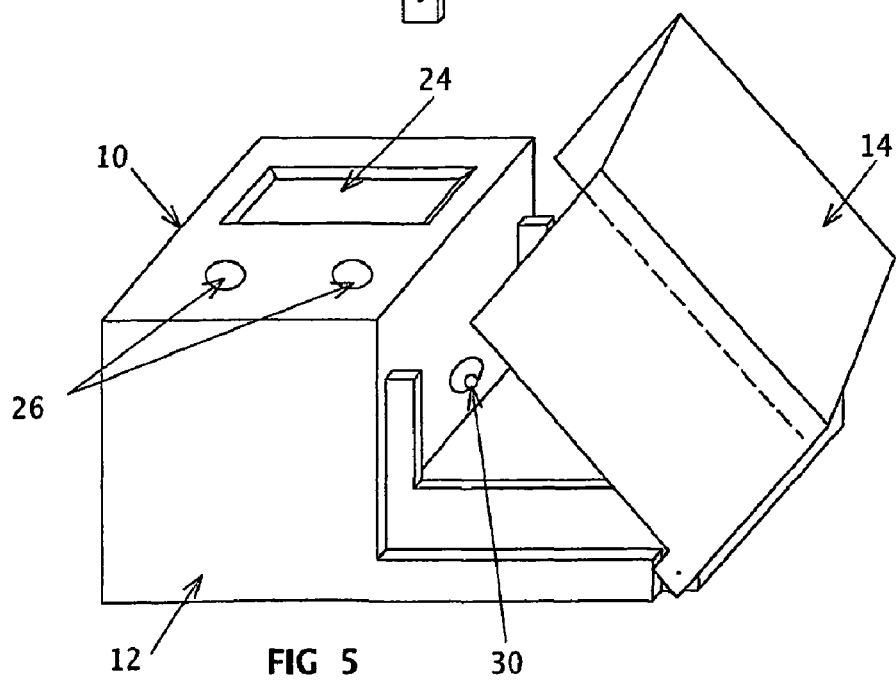
FIG. 5 is a schematic view of the apparatus of FIG. 1 fitted with the lid of FIG. 4.
Figure 6:
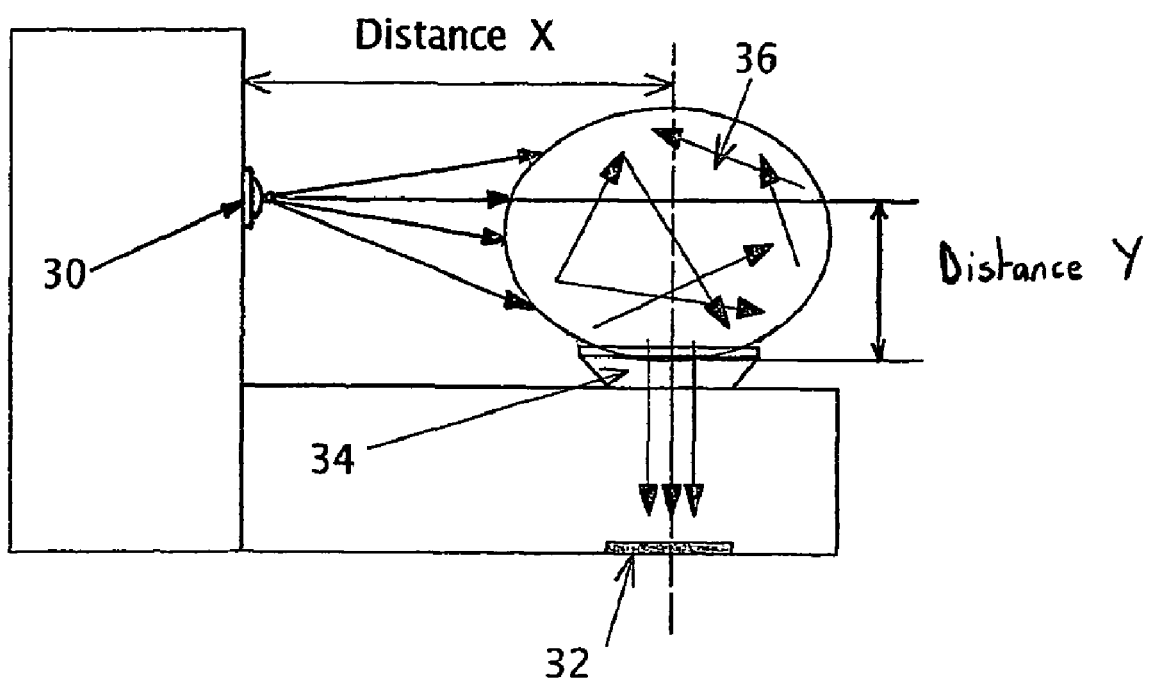
FIG. 6 is a schematic cross section through an apparatus in accordance with the present invention, part of the apparatus omitted for clarity, in use determining the viability of an egg.

In use, the lid 14 of the apparatus 10 is opened and an egg 36 (see FIG. 6) who's viability is to be determined is placed on the holder 34. The lid 14 is closed, placing the egg 34 in darkness and shielding it from IR. One of the buttons 26 on the housing 12 is pressed and, under control of electronic circuitry (not shown) in the second section 22, source 30 is activated and emits IR radiation 38 toward the egg 34 continuously until the apparatus is de-activated by the user. Upon reaching the egg 34 part of the radiation 38 is reflected off the shell of the egg 34 and part passes through the shell into the inside of the egg. It will be noted that the holder 34 inhibits radiation that has been reflected from the outside of the egg from being detected by the detector 32. As shown in FIG. 5 some of radiation 38 is repeatedly reflected off the inner side of the shell, some passes straight through and some is ultimately reflected through 90.degree. i.e. in the direction of detector 32. Upon leaving the egg 34 it is likely that some radiation 38 passes across the allantois (not shown in FIG. 6) inside the shell, and when in the early stages of incubation across the yolk sac containing the vitelline vessels. As described above, the allantois is responsible for intake of oxygen and expulsion of $CO_2$ from the egg as part of the respiratory cycle of the developing animal. Blood vessels inside this membrane continually swell and contract under the action of the animal's heart. Accordingly, as IR radiation 38 passes across this structure, some has to pass through more blood (when the blood vessels are swollen or swelling) and some passes through less blood (when the blood vessels are contracted or contracting). This results in a cyclical variation in the intensity of the IR radiation leaving the egg 36 that is a direct function of the animal's heart rate. The electrical output signal from the detector 32 also varies in the same way, the variation being of the order of approximately 0.2 mV to 1 mV. It is believed that is it is the blood vessels in the allantois that are primarily responsible for causing the cyclical variation in intensity of received infra-red. However, it might be possible that other structures are responsible for the cyclical variation, particularly the vitelline vessels when the egg is in the early stages of incubation and the yolk sac is still large.

Figure 7:
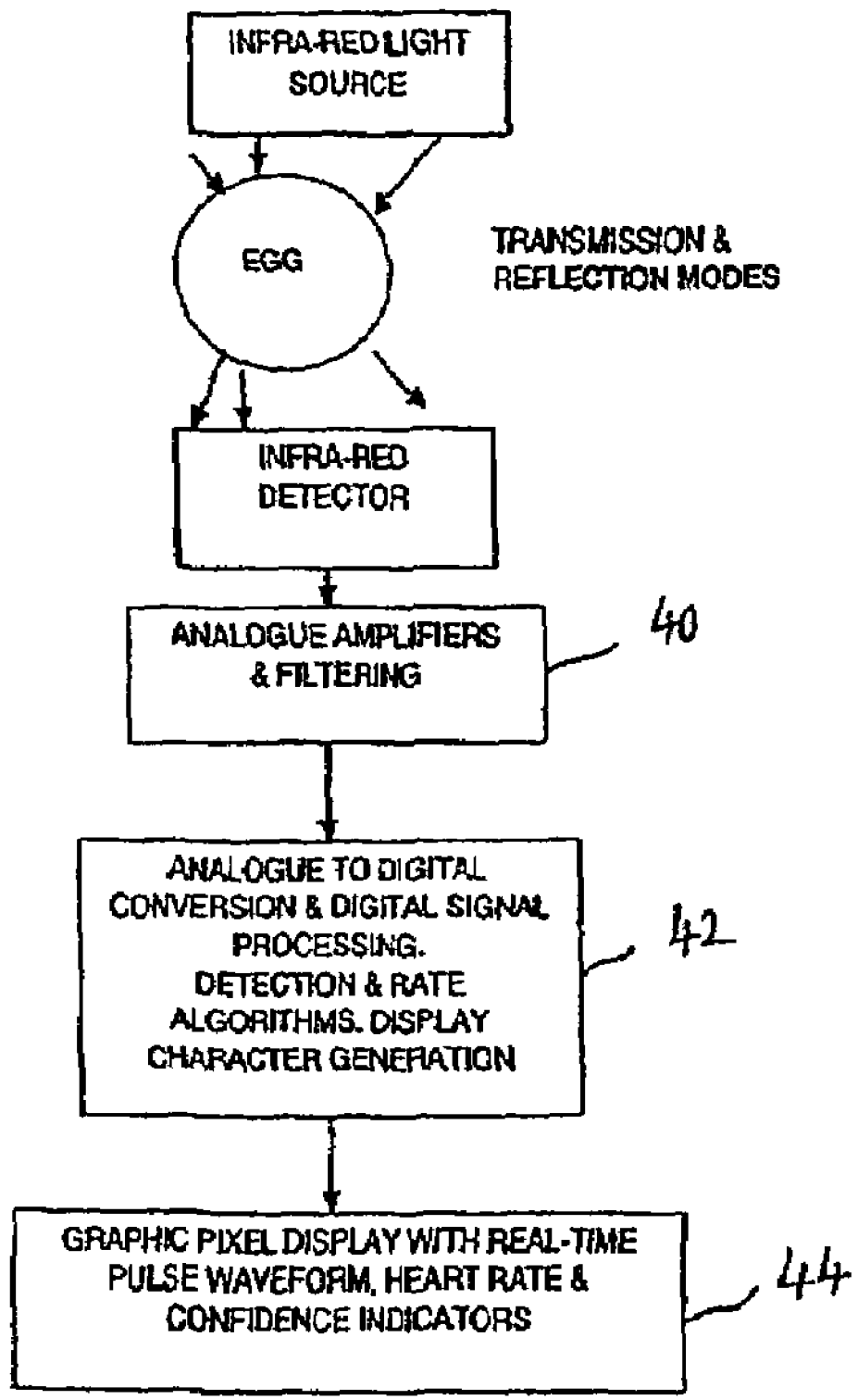
FIG. 7 is a flow diagram showing the steps of a method in accordance with the present invention.

Referring to FIG. 7 the output signal from the detector 32 is processed by electronic processing equipment located in the first section 20 of the housing 12. The signal is first amplified and then filtered at stage 40.

Figure 8:
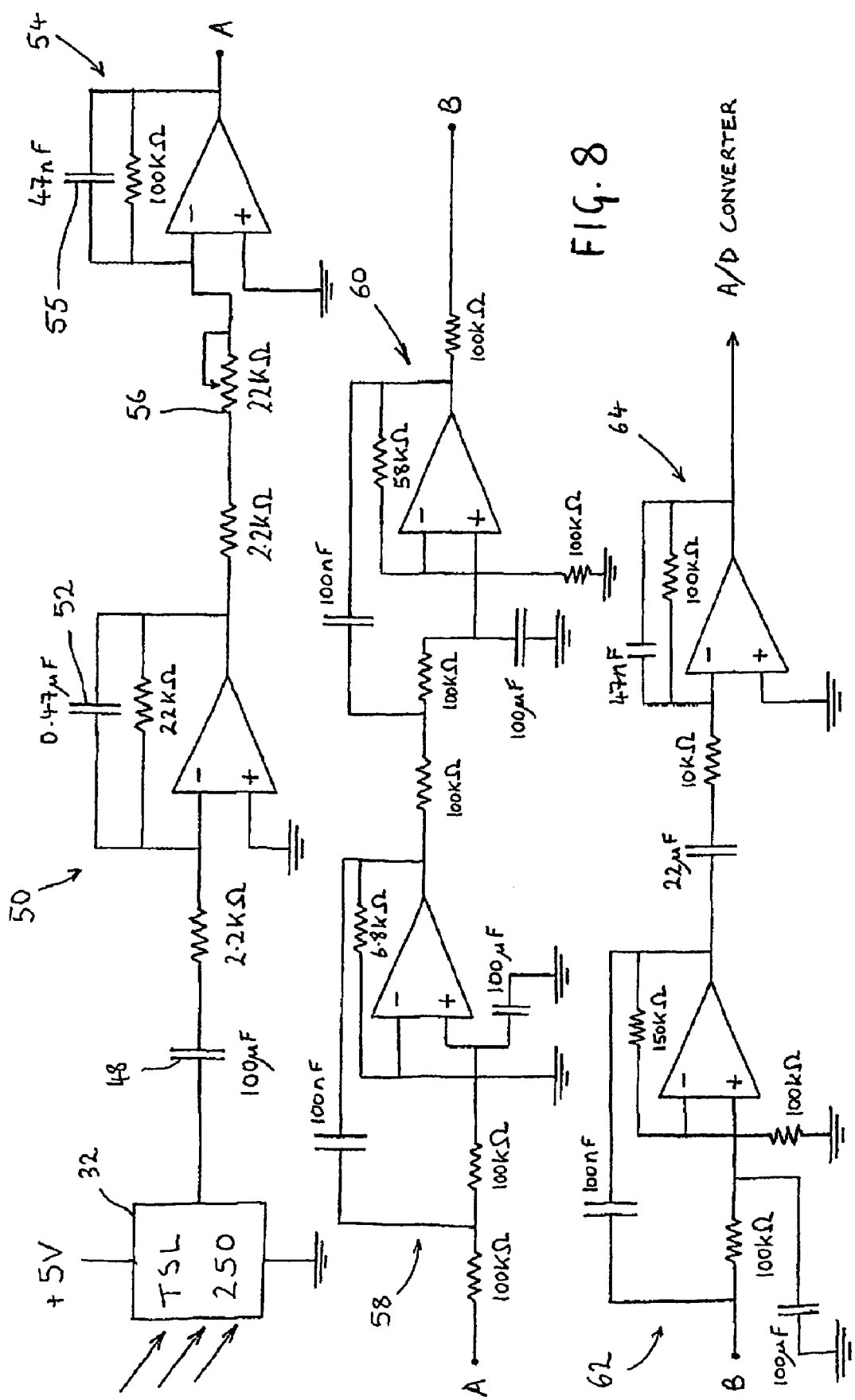
FIG. 8 is a circuit diagram of the amplification and filtering stages an apparatus in accordance with the present invention.

Stage 40 is shown in greater detail in FIG. 8. The output signal from the detector is of the order of approximately 200 mV upon which the time varying voltage of the order of a few mV is superimposed as described above. It is this time varying signal that the circuitry is designed to extract and amplify. The output signal first passes through a capacitor 48 to extract the time varying part of the signal. This time varying signal passes to a first gain stage 50 that applies a gain of 10 and also filters the signal with the capacitor 52. The capacitor 52 acts as a low pass filter with a filter corner frequency of 15 Hz i.e. the 15 Hz component of the input signal is reduced by 3 dB at this stage. 15 Hz corresponds to a heart rate of approximately 900 beats per minute, over which it is unlikely any animal's heart will beat, but also well below the 50 Hz signal generated by mains electricity. The signal then passes to a second gain stage 54 that applies a gain of between 4.13 and 45.45, depending on the value of variable resistor 56 (variable between 0 and 22 k.OMEGA.). The signal is also filtered at stage 54, the capacitor 55 being a low pass filter with a filter corner frequency of 33 Hz i.e. the 33 Hz component of the input signal is reduced by 3 dB at this stage. Because of electrical interference in the wires generated for example by induction from mains power lines it is necessary to further filter the signal; if the signal is not further filtered the time varying signal corresponding to the variation in intensity of the received IR would be totally drowned out by interference and noise. Accordingly, the signal then passes through a first filter stage 58 that applies a gain of 1.068, onto a second filter stage 60 that applies a gain of 1.58 and onto a third filter stage 62 that applies a gain of 2.50. Each filter stage is a low pass filter having a filter corner frequency set at 16 Hz i.e. the 16 Hz component of the input signal is reduced by 3 dB at each stage. Having been filtered, the signal passes through a final third gain stage 64 that applies a gain of 10 and a final low pass filtering of the signal with a corner frequency at 33 Hz.

Accordingly the overall gain on the time varying signal is between 1742 and 19180 remembering that this is because of the variable resistor 56, and the signal has been filtered at 24 dB per octave (mainly due to the effect of filtering at stages 50, 58, 60 and 62). In the actual apparatus made by the applicant the variable resistor 56 can be adjusted at the point of manufacture and is set to give the maximum gain. However, it is not adjustable by the user. The signal then leaves this section of the apparatus and moves onto the analogue to digital converter.

Referring again to FIG. 7 at stage 42 the signal is converted from analogue to digital and processed by a microcontroller (not shown). The steps of the digital signal processing are shown in greater detail in FIG. 9. The microcontroller is programmed to set up a band stop filter 84, that is it looks for that part of the signal having voltage amplitude greater than a preset voltage and that part of the signal having voltage amplitude lower than a preset voltage. The values of the band stop filter are between 2.0V and 2.9V. The time varying signal with which the apparatus is concerned is periodic by nature and when an egg is appropriately positioned the peaks 86, 88 of this signal will appear at either side of the band stop filter. Random error noise 90 will also occasionally appear at either side of the band stop filter; however, the algorithms programmed into the microcontroller are designed to extract the periodic signal and reject signals generated by random error noise that may not be hidden by the band stop filter.

Figure 9:
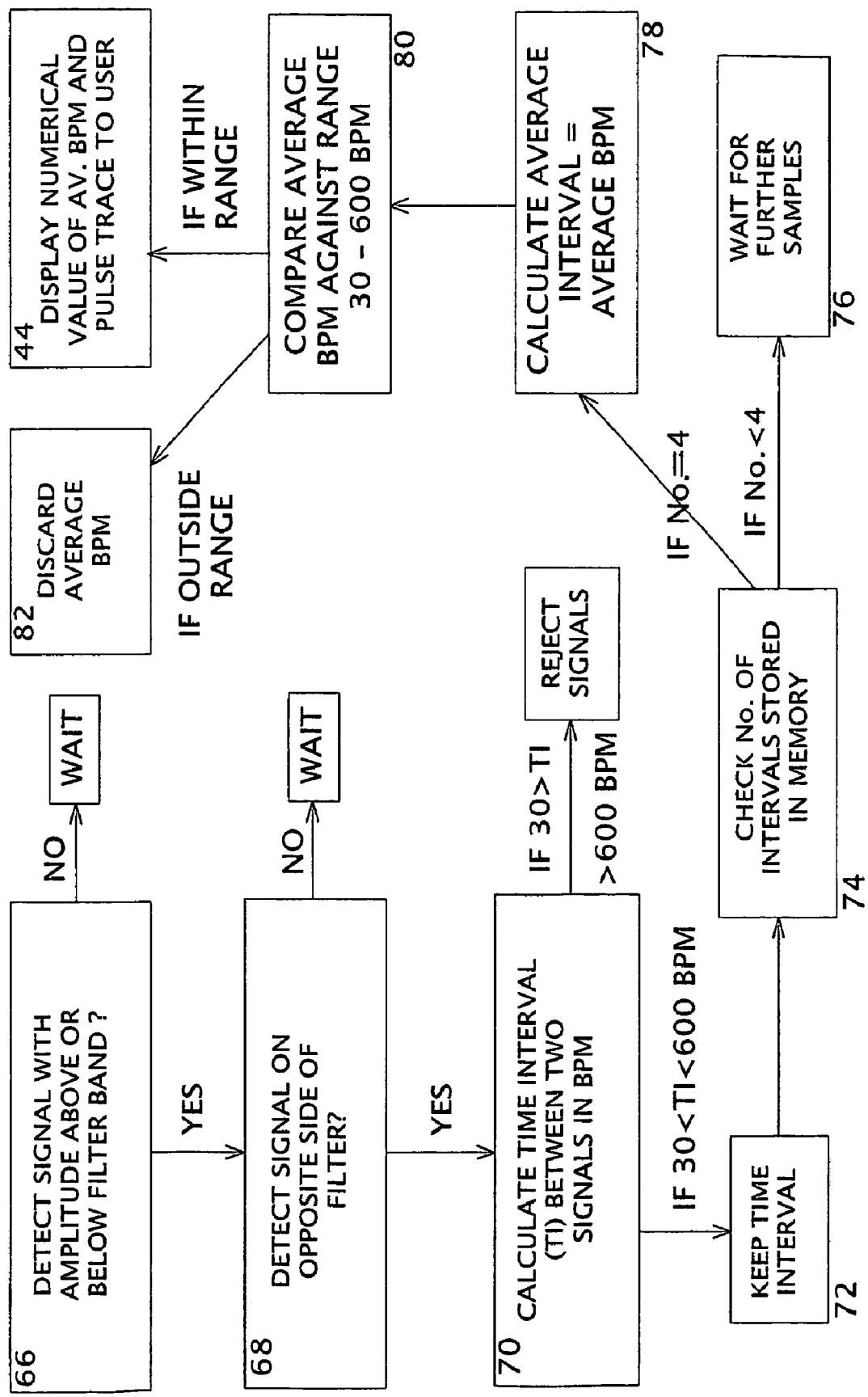
FIG. 9 is a block diagram of the algorithm used to manipulate the amplified output signal of the detector used in the apparatus of the invention.
Figure 10:
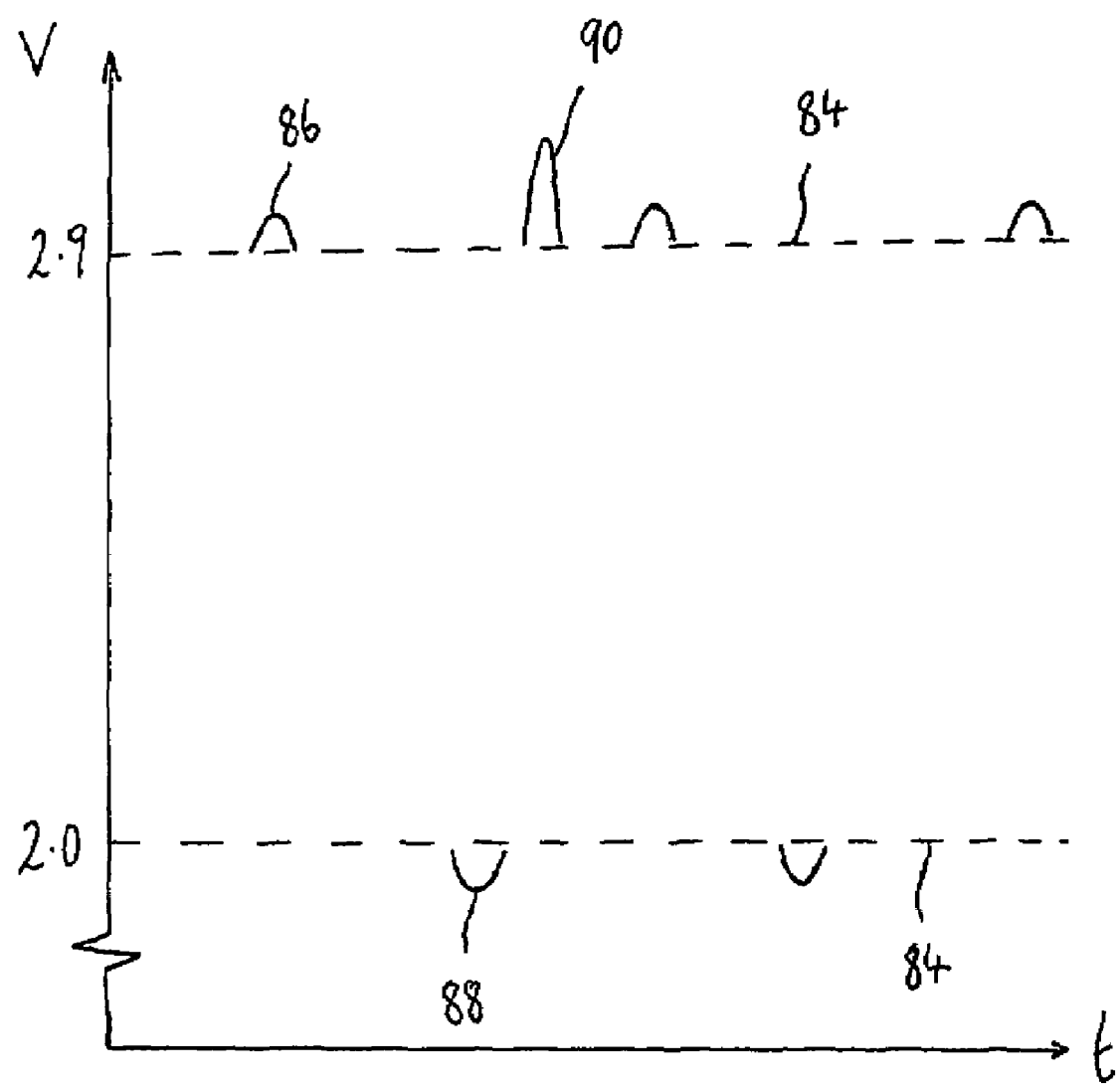
FIG. 10 is a schematic graph showing the method of detecting the cyclical variation in intensity of light received by the detector.

Referring to FIGS. 9 and 10 the first step 66 of the algorithm involves monitoring the band stop filter 84 and waiting for a signal to appear at either side. This monitoring is continuous. Whilst the algorithm is waiting for its first pair of signals 86, 88 the user sees a flat trace on the display and the numerical value of beats per minute displayed to the user is zero. When a first signal 86 does appear, the algorithm moves to step 68 in which it looks for a second signal 88; if it does not detect one it simply continues to wait whilst still monitoring. If the algorithm does detect a second signal 88 it moves to step 70 in which the time interval in beats per minute (bpm) is calculated between the detection of the first signal 86 and detection of the second signal 88. In the same stage the algorithm checks whether the calculated time interval falls within the range 30 to 600 bpm; if it does not the signals are rejected, whereas if it does the algorithm moves to step 72 in which the time interval is stored in the microcontroller's memory. At step 74 the algorithm checks the number of intervals that are stored in memory. If the number is less than four, it waits for further time intervals to be received at step 76. If the number is equal to four the algorithm calculates the average bpm from the four intervals at step 78. Using four intervals to calculate the average bpm is useful as this reduces the chance of noise affecting the result. A further advantage is that the average bpm will vary more gradually than a real time display of the bpm that may fluctuate rapidly. Finally, the algorithm checks that the calculated average bpm lies in the range 30 to 600 bpm at stage 80 (an animal's heart rate is unlikely to go above 600 bpm; at present a high heart rate that the applicant has measured was 250 bpm in a chicken egg (bantam)). If it is not, the calculated average is discarded at stage 82. If it is in the range the numerical value of bpm is displayed to the user on display 24 at stage 44 (see FIG. 7) together with a trace of voltage versus time that represents the heart rate of the animal in the egg. The trace is generated from the actual output signal, although it could be generated from the calculated average bpm. However, using the output signal enables the user to see if the apparatus has generated a spurious result, for example if there is a lot of repetitive noise in the signal. It should be noted that the microcontroller only ever stores a maximum of four intervals. When a new interval is received the oldest interval is removed to make room for the new interval. In this manner the information displayed to the user is always the latest and effectively provides a real time display of the heart rate of the animal.

Figure 11:
FIGS. 11, 12 and 13 show various examples of traces of voltage (Y-axis) against time (X-axis) that can been seen on a screen of an apparatus in accordance with the present invention.
Figure 12:

If no cyclical variation is obtained from the detector the display 24 indicates that the egg is not viable and the trace shows a flat line indicating IR being received by the detector 32 at a constant rate (FIG. 11). If the egg is viable a trace similar to that shown in FIG. 12 is seen.

Figure 13:

The applicant has found that, even if the egg is viable, it is not always possible to obtain a satisfactory output from the detector 32. In particular, this occurs if the animal moves inside the egg or if the infra-red does not pass through a sufficiently big blood vessel as it exits the egg. If the animal is moving the trace on display 24 is rapid, erratic and the pulse is exaggerated. If the egg is in a bad position, the trace shows faint pulse line i.e. greatly reduced in magnitude (FIG. 13), but not a flat line as with a non-viable egg. In this situation, the algorithms at stage 42 cause the display to show a signal to the user either that animal is moving or that the egg is badly positioned which prompts the user to wait or re-position the egg. A user may need to re-position the egg between 1 and 3 times to be sure that an egg is not viable, and preferably repeat the process at several intervals of 24 hours in order to be completely sure that the egg is not viable. Although the apparatus indicates the viability almost immediately, the eggs of some species are too valuable to discard on the basis of one reading. The electronic processing equipment continually monitors the received signal and as soon as a viable signal is received the heart rate trace and beats per minute are displayed.

The applicant has also found that the best signal is obtained when the radiation impinges on an egg from its side i.e. substantially perpendicular to its longitudinal axis, and the detector 32 is located below the egg with its detection axis substantially perpendicular to the axis of the source 30. However, in the early stages of development of the egg, the detector 30 and source 32 can be placed anywhere around the egg or the egg placed at any orientation within the apparatus 10 to obtain a signal. When the egg is more developed, the animal occupies so much of the volume of the egg that only a narrow range of positions obtains a satisfactory signal. One of these positions is shown in FIG. 4 and is further advantageous because the egg can be readily supported in this position. The applicant has also found that when nearly fully developed, the best signals are obtained when the radiation impinges on the rounded or "blunt" end of the egg and passes through the air sack inside, thus still passing through the structures mentioned above but not being obstructed by the animal.

Important variations of the above embodiment are that the electronic processing equipment may be separate from the box in which the egg is placed i.e. the first section 20 may be separate from the second section 22. If no signal is obtained from the detecting means, the display 24 may prompt the user to move the egg and/or re-activate the apparatus so that the viability is determined over a number of interrogations, thus minimising the chances of error.

The apparatus may be incorporated into known incubators to provide an "all-in-one" arrangement for incubating eggs.

The apparatus described in the preferred embodiment is designed to be hand-held and portable. However, this is not essential.

The invention claimed is:

1. An apparatus for determining the viability of an egg, which apparatus comprises, an emitter and a detector, the arrangement being such that, in use, said emitter can emit electromagnetic radiation that impinges on the blunt end of the egg, and the detector is positioned to detect at least a part of said electromagnetic radiation that has passed through the egg, the apparatus further comprising electronic processing equipment for processing an output signal of the detector to determine whether there is a superimposed cyclical variation in the intensity of the radiation leaving the egg corresponding to action of a heart, the existence of said superimposed cyclical variation indicating that the egg is viable, characterised in that said emitter can emit electromagnetic radiation at infra-red wavelength(s) but not at optical wavelengths and said detector can detect infra-red radiation leaving said egg, whereby said superimposed cyclical variation is detectable up until the animal hatches from the egg.

2. An apparatus as claimed in claim 1, wherein said electronic processing equipment is configured to process said output signal such that it may be used to provide a visual display trace on which any superimposed cyclical variation is apparent.

3. An apparatus as claimed in claim 1, wherein said electronic processing equipment can determine a heart rate and provide a heart rate output signal suitable for displaying a numerical indication of the heart rate on a display.

4. An apparatus as claimed in claim 1, wherein the means for processing extracts only variation in the output signal.

5. An apparatus as claimed in claim 1, wherein said electronic processing equipment can extract the time interval between successive points in the superimposed cyclical variation in order to calculate a heart rate therefrom.

6. An apparatus as claimed in claim 5, wherein said electronic processing equipment can compare the calculated heart rate against a predetermined range to ensure that the calculated heart rate lies within the range to inhibit the effect of random noise.

7. An apparatus as claimed in claim 5, wherein said electronic processing equipment can extract a plurality of time intervals, and is able to calculate an average time interval and an average heart rate therefrom.

8. An apparatus as claimed in claim 7, wherein said electronic processing equipment can compare the calculated average heart rate against a predetermined range to ensure that the calculated average heart rate lies within the range to inhibit the effect of random noise.

9. An apparatus as claimed in claim 1, wherein said emitter emits electromagnetic radiation over a limited angle.

10. An apparatus as claimed in claim 9, wherein said limited angle is adjustable.

11. An apparatus as claimed in claim 1, wherein the emitter emits electromagnetic radiation in the wavelength range 720 nm to 940 nm.

12. An apparatus as claimed in claim 1 wherein the emitting means emit electromagnetic radiation predominantly at a wavelength of 875 nm.

13. A method of determining the viability of an egg, which method comprises the steps of:
    (1) emitting electromagnetic radiation from an emitter toward the blunt end of said egg;
    (2) detecting at least a part of said electromagnetic radiation that has passed through the egg with a detector and generating an output signal therefrom; and
    (3) processing said output signal to determine whether there is a superimposed cyclical variation in the intensity of the radiation leaving the egg corresponding to action of a heart, the existence of said superimposed cyclical variation indicating that the egg is viable;

characterised in that step (1) is performed by emitting electromagnetic radiation at infra-red wavelength(s) but not at optical wavelengths toward said egg and step (2) is performed by detecting electromagnetic radiation at infra-red wavelengths that has passed therethrough, whereby said superimposed cyclical variation is detectable up until the animal hatches from the egg.

14. A method as claimed in claim 13, further comprising the step of providing a visual display trace on which any superimposed cyclical variation is apparent.

15. A method as claimed in claim 13, further comprising the step of processing said output signal to determine a heart rate and displaying a numerical value of the heart rate to a user.

16. A method as claimed in claim 13, further comprising the step of extracting only variation in the output signal.

17. A method as claimed in claim 13, further comprising the step of extracting the time interval between successive points in the cyclical variation in order to calculate a heart rate therefrom.

18. A method as claimed in claim 17, further comprising the step of comparing the calculated heart rate against a predetermined range to ensure that the calculated heart rate lies within the range to inhibit the effect of random noise.

19. A method as claimed in claim 17, further comprising the step of extracting a plurality of time intervals, and calculating an average time interval and heart rate therefrom.

20. A method as claimed in claim 19, further comprising the step of comparing the calculated average heart rate against a predetermined range to ensure that the calculated average heart rate lies within the range to inhibit the effect of random noise.

21. A method as claimed in claim 13, wherein step (2) is carried out by emitting infra-red over a limited angle.

22. A method as claimed in claim 21, wherein the limited angle is adjustable.

23. A method as claimed in claim 13, wherein step (2) is carried out by emitting electromagnetic radiation in the wavelength range 720 nm to 940 nm.

24. A method as claimed in claim 23, wherein the emitting means emit electromagnetic radiation predominantly at a wavelength of 875 nm.

* * * * *